United States Patent
Konno et al.

(10) Patent No.: US 11,172,861 B2
(45) Date of Patent: Nov. 16, 2021

(54) DETECTION DEVICES AND MONITORING SYSTEMS INCLUDING DETECTION DEVICES

(71) Applicant: NIHON KOHDEN CORPORATION, Tokyo (JP)

(72) Inventors: Norihito Konno, Tokorozawa (JP); Fumiyuki Matsumura, Tokorozawa (JP); Hirohiko Ikeya, Tokorozawa (JP)

(73) Assignee: Nihon Kohden Corporation, Tokyo (JP)

(*) Notice: Subject to any disclaimer, the term of this patent is extended or adjusted under 35 U.S.C. 154(b) by 183 days.

(21) Appl. No.: 15/818,520

(22) Filed: Nov. 20, 2017

(65) Prior Publication Data

US 2018/0150612 A1 May 31, 2018

(30) Foreign Application Priority Data

Nov. 25, 2016 (JP) .............................. JP2016-229042

(51) Int. Cl.
*A61B 5/00* (2006.01)
*A61B 5/361* (2021.01)
(Continued)

(52) U.S. Cl.
CPC ............. *A61B 5/361* (2021.01); *G16H 40/67* (2018.01); *G16H 50/20* (2018.01); *A61B 5/002* (2013.01);
(Continued)

(58) Field of Classification Search
CPC ... A61B 5/0002; A61B 5/0004; A61B 5/0006; A61B 5/0008; A61B 5/0015; A61B 5/002; A61B 5/022; A61B 5/0224; A61B 5/0205; A61B 5/02055; A61B 5/024; A61B 5/02438; A61B 5/0245; A61B 5/02455; A61B 5/0255; A61B 5/0402; A61B 5/0432; A61B 5/04325; A61B 5/1112; A61B 5/1113; A61B 5/1115; A61B 5/1116;
(Continued)

(56) References Cited

U.S. PATENT DOCUMENTS

| 2005/0191716 | A1* | 9/2005 | Surwit | ................ | G06F 19/3456 435/13 |
| 2007/0010256 | A1* | 1/2007 | Klabunde | ............ | A61B 5/0006 455/452.2 |

(Continued)

FOREIGN PATENT DOCUMENTS

| JP | 2001078974 A | 3/2001 |
| JP | 2007007015 A | 1/2007 |

(Continued)

OTHER PUBLICATIONS

English translation of JP Office Action for Application No. 2016-229042, dated Aug. 4, 2020.

*Primary Examiner* — Eugene T Wu
(74) *Attorney, Agent, or Firm* — Dorsey & Whitney LLP

(57) ABSTRACT

Examples described herein include detection devices and systems which may provide monitoring in accordance with an analysis mode which may be selected in accordance with a severity of disease of the user. Analysis modes used by detection devices described herein may further be changed in accordance with user and/or environmental conditions.

21 Claims, 8 Drawing Sheets

(51) Int. Cl.
*G16H 50/20* (2018.01)
*G16H 40/67* (2018.01)
*A61B 5/332* (2021.01)
*A61B 5/01* (2006.01)
*A61B 5/11* (2006.01)

(52) U.S. Cl.
CPC ........... *A61B 5/0006* (2013.01); *A61B 5/0008* (2013.01); *A61B 5/0022* (2013.01); *A61B 5/01* (2013.01); *A61B 5/1112* (2013.01); *A61B 5/1118* (2013.01); *A61B 5/332* (2021.01); *A61B 5/7475* (2013.01)

(58) Field of Classification Search
CPC ... A61B 5/1117; A61B 5/1118; A61B 5/4842; A61B 5/68; A61B 5/6801; A61B 5/6802; A61B 5/6823; A61B 5/746; A61B 5/7465; A61B 5/747; A61B 2505/03; A61B 2503/07
See application file for complete search history.

(56) References Cited

U.S. PATENT DOCUMENTS

| | | | | |
|---|---|---|---|---|
| 2008/0221399 | A1* | 9/2008 | Zhou | A61B 5/021 600/301 |
| 2010/0063365 | A1* | 3/2010 | Pisani | A61B 5/0006 600/301 |
| 2014/0171749 | A1* | 6/2014 | Chin | A61B 5/0015 600/300 |
| 2015/0305689 | A1 | 10/2015 | Gourmelon et al. | |
| 2016/0262641 | A1* | 9/2016 | Kurzenberger | A61B 5/02438 |

FOREIGN PATENT DOCUMENTS

| | | |
|---|---|---|
| JP | 2009189570 A | 8/2009 |
| JP | 2012085906 A | 5/2012 |
| JP | 2016507256 A | 3/2016 |

* cited by examiner

DETECTION DEVICES AND MONITORING SYSTEMS INCLUDING DETECTION DEVICES

CROSS-REFERENCE TO RELATED APPLICATION(S)

This application claims the benefit under 35 U.S.C. § 119 of the earlier filing date of Japanese application 2016-229042, filed Nov. 25, 2016. The priority Japanese application is hereby incorporated by reference in its entirety for any purpose.

TECHNICAL FIELD

Examples described herein relate to a detection device which may be used for patient monitoring, and a monitoring system including the detection device.

BACKGROUND

Currently, a survival rate for heart attacks caused by arrhythmia is still low. Patients may vary in the severity of their condition, and patients' condition or environment may change over time.

Existing systems of monitoring patients generally are designed to utilize a particular fixed monitoring methodology.

DETAILED DESCRIPTION

Figure 1:
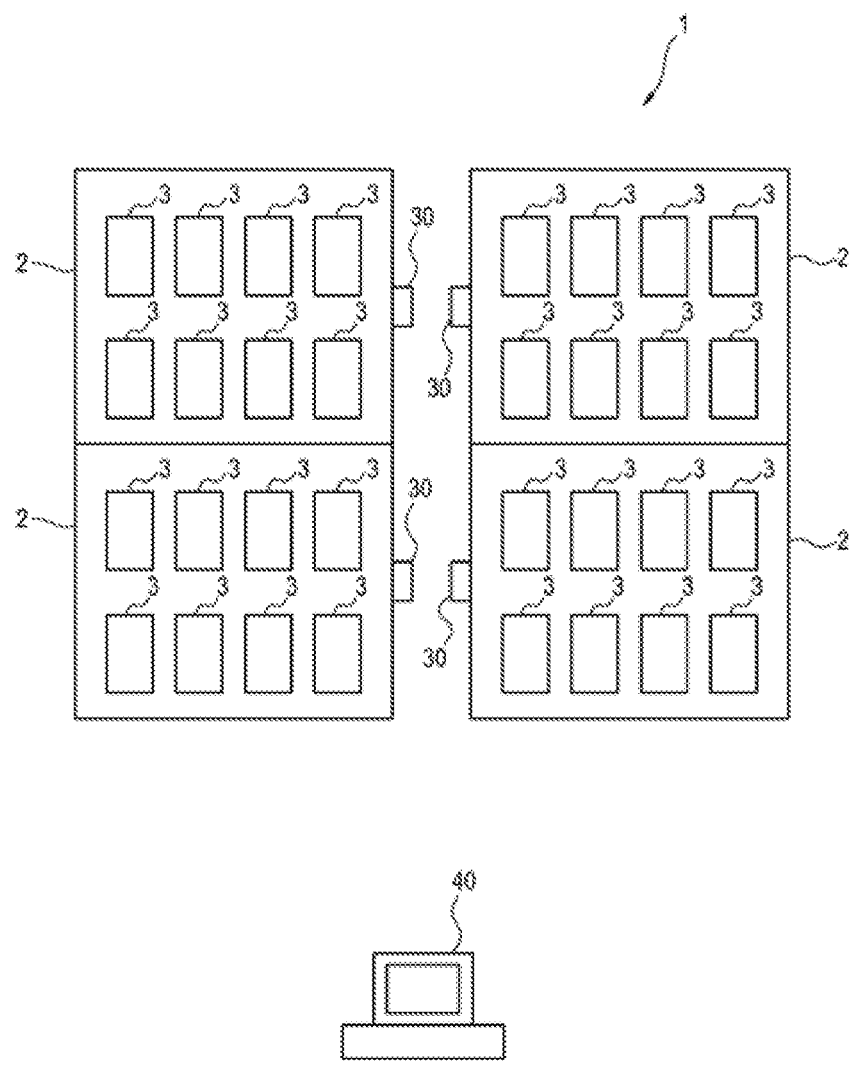
FIG. 1 is a schematic illustration of a ward which may utilize a monitoring system described herein.

Certain details are set forth herein to provide an understanding of described embodiments of technology. However, other examples may be practiced without various of these particular details. In some instances, well-known circuits, control signals, timing protocols, and/or software operations have not been shown in detail in order to avoid unnecessarily obscuring the described embodiments. Other embodiments may be utilized, and other changes may be made, without departing from the spirit or scope of the subject matter presented here.

Examples of detection devices and monitoring systems are described herein which may be capable of assisting in providing medical services suitable for respective patients.

An example detection device described herein may be carried (e.g., worn) by a user (e.g., a patient). The example detection device may include measurement circuitry configured to measure a biological signal of the user while the detection device is being carried by the user. The detection device may include at least one processor which may analyze the biological signal. The detection device may support a number of analysis modes, and the processor may analyze the biological signal and/or transmit measurement results in accordance with a selected one of the modes. The detection device may include storage (e.g., a memory) which may store data for the analysis modes. The detection device may include a transmitter which may transmit measurement results processed by the processor to another computing device (e.g., a communication device). The analysis mode used may be selected from multiple predetermined analysis modes in accordance with a severity of disease of the user.

Accordingly, a medical worker or other user may select an analysis mode for devices described herein in accordance with severity of disease of the user. The selection may be made, for example, when attaching the detection device to a body surface of the user (for example, a patient). A medical worker may select an analysis mode in which the number of analysis items is small for users having relatively a low severity of disease, while the medical worker may select an analysis mode in which the number of analysis items is large for a user having a relatively high severity of disease. These devices, methods, and/or systems, may assist in providing individualized medical monitoring.

An example monitoring system described herein may include a plurality of detection devices described herein, a plurality of computing devices (e.g., communication devices) which may communicate with the detection devices, and a centralized management device which may communicate with the plurality of communication devices. The centralized management device may include a display on which a plurality of analysis results transmitted via the communication devices may be displayed (e.g., in a list).

Accordingly, examples described herein may assist in providing medical services suitable for respective patients, may provide improved monitoring, for example, in a ward where multiple patients having heart disease may be hospitalized, and may reduce loads of medical workers.

FIG. 1 is a schematic illustration of a ward which may utilize a monitoring system described herein. The ward 1 includes a number of rooms 2. Each of the rooms 2 may have, a number of stations 3. FIG. 1 further illustrates computing devices 30 and centralized management device 40.

While referred to as ward 1 and rooms 2 in FIG. 1, the ward 1 and rooms 2 may generally refer to a location and sub-locations in which multiple users (e.g., patients may be located). Examples of locations and sub-locations include, but are not limited to, buildings, houses, hospitals, businesses, amusement parks, vehicles (e.g., planes, cars, buses), cities, neighborhoods, rooms, floors, streets, and other areas.

Each of the rooms 2 may have a number of stations 3 for individual users. any number of users may be located in each room or sub-location (e.g., 1, 2, 3, 4, 5, 6, 7, 8, 9, 10, or more users). The stations 3 may be implemented using beds, desks, chairs, lockers, purses, bags, or other locations or items associated with a user. Generally, each station 3 may be associated with a single user, although in some examples a station may be associated with multiple users. Examples of detection devices described herein may be carried by (e.g., attached to, supported by, worn by) individual users.

A computing device may be provided to communicate with a plurality of detection devices. Computing devices 30 are shown in FIG. 1. In the example of FIG. 1, there may be one computing device 30 for each room 2. In other examples, there may be multiple computing devices in a single room. In other examples, a computing device may communicate with detection devices in multiple rooms.

The computing devices 30 may be implemented using, one or more receivers which may include, for example, in one or more computers, servers, desktops, laptops, tablets, smart phones, routers, appliances, or equipment.

Multiple computing devices may be in communication with a centralized management device 40. The centralized management device 40 may be implemented, for example, using, one or more receivers which may include, for example, in one or more computers, servers, desktops, laptops, tablets, smart phones, routers, appliances, or equipment. In some examples, the centralized management device may be implemented at a nurses' station where medical workers are on call.

Generally, the computing devices 30 (e.g., communication devices) may be positioned proximate a subset of users of detection devices described herein. The centralized management device 40 can communicate with the detection devices 10 attached to the users in each sickroom 2 through the computing devices 30.

For example, the detection devices 10 may communicate with the computing devices 30 using a short-range wireless communication method (e.g., NFC (Near Field Communication) and/or BLUETOOTH). In some examples, the computing devices 30 may communicate with the centralized management device 40 using a long-range wireless communication method (e.g., through networks such as a wide area network (WAN), local area network (LAN), and/or Internet). In other examples, wired communication may be used between the computing devices 30 and the detection devices and/or between the computing devices 30 and the centralized management device 40.

Figure 2:
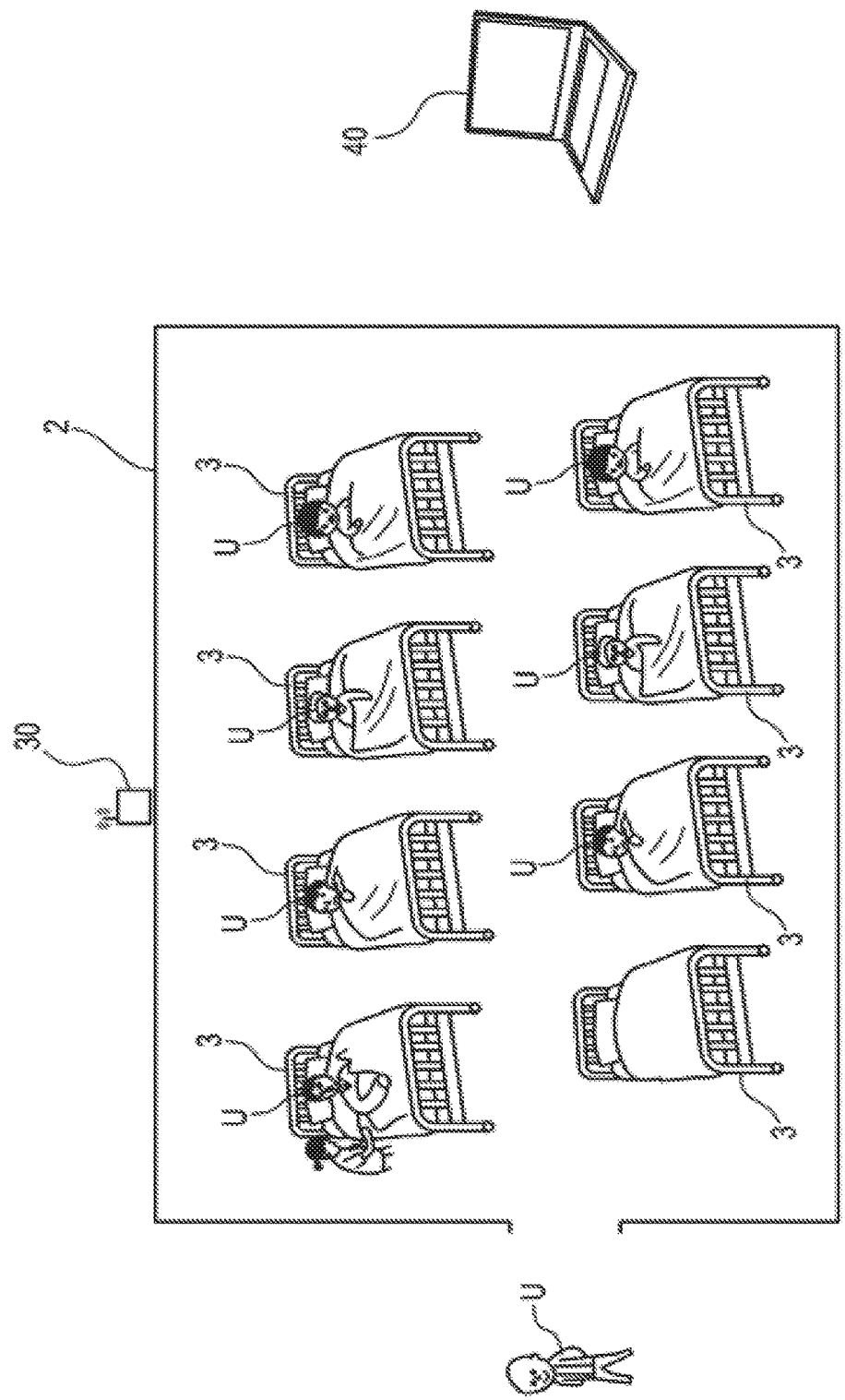
FIG. 2 is a schematic illustration of a room of FIG. 1 arranged in accordance with examples described herein.

FIG. 2 is a schematic illustration of a room of FIG. 1 arranged in accordance with examples described herein. FIG. 2 illustrates users U in a room 2. As shown, each user U may be associated with a bed 3. Each user may be carrying (e.g., wearing and/or adhered to) a detection device described herein. In the example of room 2 of FIG. 2, eight beds 3 are included in the room 2, associated eight users U. Seven users are shown in the beds, and an additional user U is illustrated walking out of the room 2. The user U walking out of the room may also be carrying (e.g., wearing and/or holding) a detection device described herein. Monitoring systems described herein may continue to monitor biological signals from users even as the users traverse monitored areas—e.g., move between rooms, between other monitored locations, etc.

Figure 3:
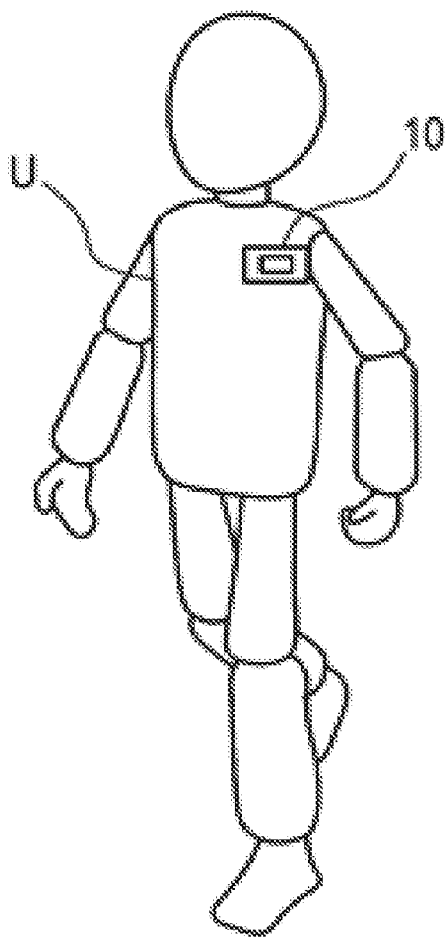
FIG. 3 is a schematic illustration of a user carrying a detection device in accordance with examples described herein.

FIG. 3 is a schematic illustration of a user carrying a detection device in accordance with examples described herein. The user U shown in FIG. 3 has a detection device 10 attached to a chest of the user.

Generally, detection devices described herein may be carried by a user in any of a variety of ways. The detection devices may, for example, be attached to the user (e.g., adhered to a body surface of the user and/or adhered to a surface of an item carried or worn by the user). Detection devices may in some examples be held or worn by the user. Detection devices may in some examples be carried by the user using, for example, a bag, a purse, or another electronic device.

In some examples, one or more components of a detection device (e.g., one or more electrodes) may be placed in contact with a body surface of the user.

Detection devices described herein may generally be positioned proximate and/or may contact any of a variety of places on the user—e.g., chest, back, forehead, finger, arm, leg, foot, toe. In some examples, a user may carry more than one detection device.

While the user in FIG. 3 is illustrated in a standing position, in some examples, users may be seated and/or lying down while carrying detection devices described herein. Users may change positions while wearing detection devices described herein.

Any of a variety of users may utilize detection devices described herein including patients, athletes, students, employees, humans, adults, children, infants, animals, and/or livestock.

Figure 4:
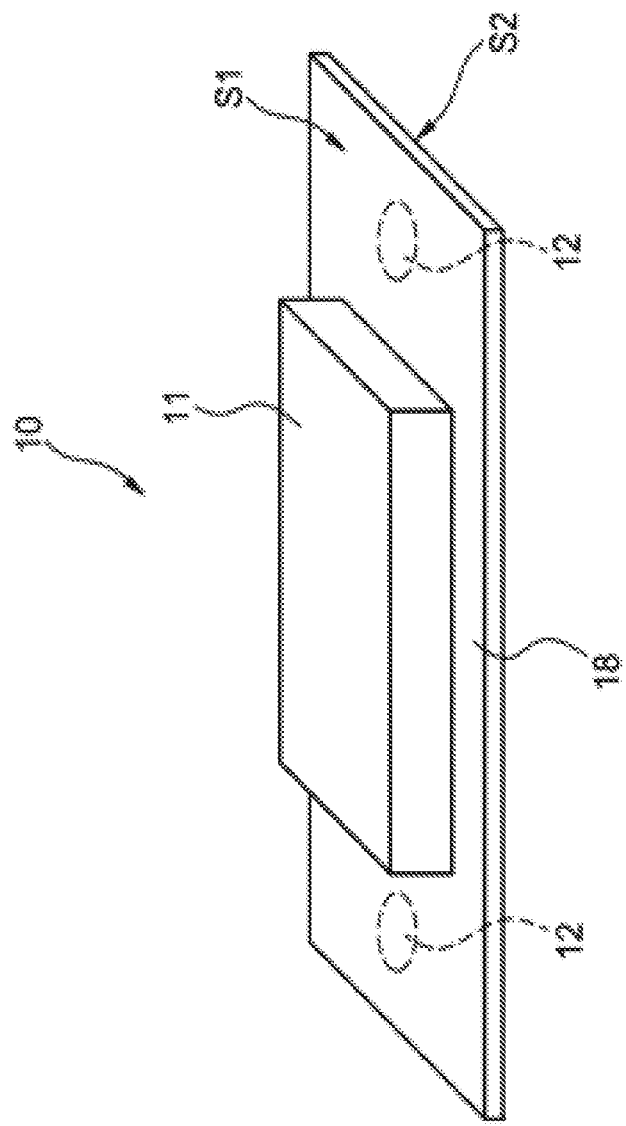
FIG. 4 is a schematic illustration of a perspective view of a detection device arranged in accordance with examples described herein.

FIG. 4 is a schematic illustration of a perspective view of a detection device arranged in accordance with examples described herein. The detection device 10 includes main body 11, substrate 18, and electrodes 12. Additional, fewer, and/or different components may be used in other examples.

The substrate 18 may be implemented using, for example, a long thin sheet, including a first surface S1 and a second surface S2 on the opposite side of the first surface S1. The substrate 18 may be carried by a user during operation of the detection device 10. For example, the substrate 18 may be adhered to a user and/or worn by a user. The substrate 18 may in some examples be implemented using a flexible and/or biocompatible material. In some examples, an outermost surface of the second surface S2 may be wholly or partially formed of a material having adhesive properties to facilitate adhesion to a user.

The main body 11 may be supported by the first surface S1 of the substrate 18. The main body 11 may include electronics as described herein including but not limited to, circuitry including one or more analog front end, processor(s), transmitter(s), and/or memory. The main body 11 may be implemented using one or more semiconductor chips, for example, and may include a housing wholly or partially enclosing electronics.

The detection device 10 may include electrodes 12 which may couple to a user during operation of the detection device 10. During operation, for example, the electrodes 12 may contact a body surface of the user (e.g., the chest, etc.). While two electrodes 12 are shown in FIG. 4, any number may be present. The electrodes 12 are provided on a second surface S2 of the substrate 18, which may be opposite a surface S1 supporting the main body 11, although other arrangements are possible. The electrodes 12 may be in electrical communication with electronics in the main body 11, e.g., through conductive lines present on the substrate 18 and/or through wireless coupling.

During operation, the electrodes 12 may be used to detect one or more biological signals of the user (e.g., an electrocardiogram).

While shown as a unitary device in FIG. 4, examples of detection devices described herein may be provided as multiple sub-units in some examples which may be in electrical communication. For example, the electrodes 12 of FIG. 4 may in some examples be provided separately from the main body 11.

The detection device of FIG. 4 is illustrated as a structure in which biological signals of the user can be measured when the electrodes 12 are in contact with a body surface of a user. In some examples, detection devices described herein may have other form factors, and may not be attached (e.g., adhered) to a body surface of a user, although the detection device may be carried by the user. For example, detection devices may be provided in the form of a pendant, a necklace, or a watch, etc.

Figure 5:
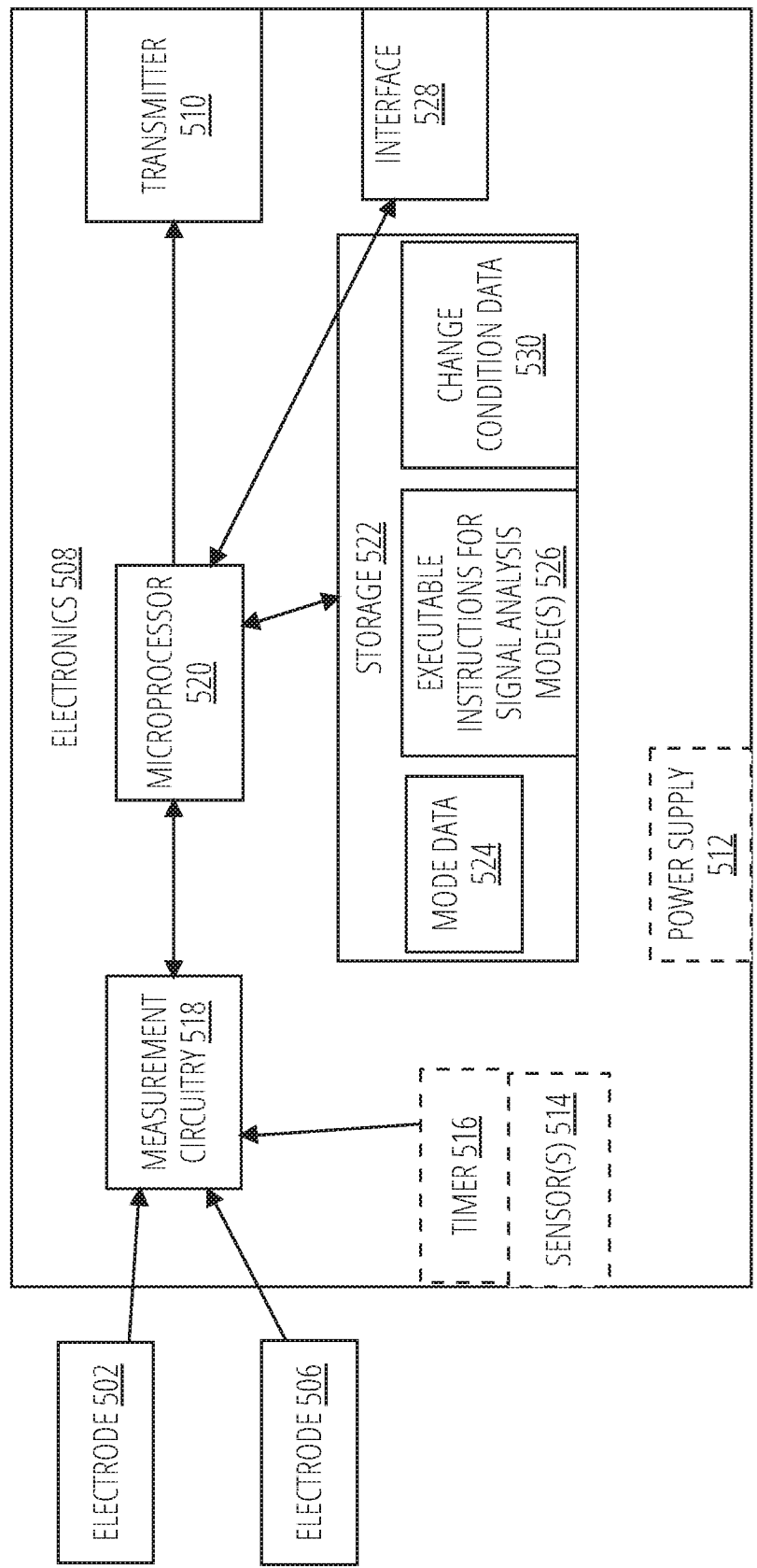
FIG. 5 is a schematic illustration of a detection device arranged in accordance with examples described herein.

FIG. 5 is a schematic illustration of a detection device arranged in accordance with examples described herein. The detection device 504 may include electrode 502, electrode 506, and electronics 508. The electronics 508 may include transmitter 510, power supply 512, sensor(s) 514, timer 516, measurement circuitry 518, microprocessor 520, storage 522, and/or interface 528. The storage 522 may store mode data 524, executable instructions for signal analysis mode(s) 526, and/or change condition data 530. Additional, fewer, and/or different components may be present in other examples. The detection device 504 may be used to implement and/or may be implemented by the detection device 10 of FIG. 1-FIG. 4 in some examples. For example, the electronics 508 may form part or all of the main body 11 of the detection device 10 of FIG. 4, and the electrode 502 and electrode 506 may be used to implement the electrodes 12 of FIG. 4.

Examples of detection devices described herein may include electrodes, such as electrode 502 and electrode 506 of FIG. 5. Any number of electrodes may be used. The electrodes may be in direct contact with a body surface of a user (e.g., skin of a user) during operation. The electrodes may detect a biological signal of a user (e.g., an electrocardiogram).

Examples of detection devices described herein may include measurement circuitry, such as measurement circuitry 518 of FIG. 5. For example, the measurement circuitry 518 may be implemented using an analog front end (AFE). The measurement circuitry 518 may be electrically coupled to the electrodes (e.g., using one or more conductive lines, traces, wires, etc.). The measurement circuitry 518 may measure a biological signal of a user during use (e.g., when the detection device is carried by the user). The measurement circuitry 518 may measure and/or condition the biological signal received by the electrodes—for example the measurement circuitry 518 may provide filtering, amplification, and/or may convert an analog biological signal received from the electrodes into a digital signal. The measurement circuitry 518 may be in electronic communication with the microprocessor 520 and may provide biological signals to the microprocessor 520.

Examples of detection devices described herein may include one or more processors, such as microprocessor 520. While microprocessor 520 is shown in FIG. 5, any number or variety of processors may be used, including one or more central processing units (CPUs), controllers, multi-core processors, and/or logic circuitry including application specific integrated circuits (ASICs) and/or field programmable gate arrays (FPGAs).

Examples of detection devices described herein may include electronic storage, such as storage 522 of FIG. 5. The storage may be implemented using, for example, one or more computer readable media (e.g., memory, read only memory (ROM), random access memory (RAM), flash, solid state drives, secure digital (SD) card, or combinations thereof).

The storage 522 may store executable instructions for signal analysis mode(s) 526 which, when executed by the microprocessor 520, may cause the detection device 504 to perform actions described herein. For example, the instructions may cause the detection device 504 to operate in accordance with a selected analysis mode of a plurality of analysis modes to analyze the biological signal and provide one or more measurement results. In this manner, the detection device 504 may be programmed to perform as described herein. The executable instructions for signal analysis mode(s) 526 may include instructions for analyzing biological signals of a user received from electrode 502, electrode 506, and/or measurement circuitry 518. The executable instructions for signal analysis mode(s) 526 may include instructions for generating one or more measurement results based on the biological signals. Any of a variety of measurement results may be generated by analyzing biological signals described herein. For example, the executable instructions for signal analysis mode(s) 526 may, in some modes, analyze whether an abnormal waveform indicative of ventricular fibrillation, atrial fibrillation, or combinations thereof, are contained in an electrocardiogram received from the electrodes and/or measurement circuitry 518.

The executable instructions for signal analysis mode(s) 526 may include instructions for transmitting measurement result(s) to one or more other computing devices. Generally, the signal analysis may be performed in accordance with a selected one of a plurality of possible modes. Each mode may specify, for example, a type and/or number of biological signal(s) to analyze, a frequency with which to analyze the signal(s) and/or to generate measurement results, and/or a frequency with which to transmit measurement results to another computing device (e.g., how frequently a measurement result may be transmitted). This information may be wholly and/or partially stored in mode data 524. For example, the mode data 524 may include data specifying the parameters for one or more modes.

The executable instructions for signal analysis mode(s) 526 may include instructions for selecting and/or changing the mode of signal analysis being used. As described herein, the mode may be selected and/or changed based on a severity of user disease, based on measurement results (e.g., generated by microprocessor 520) and/or based on other predetermined conditions. For example, a different analysis mode may be selected for a patient having a mild disease than for a patient having a severe form of the disease. For example, an analysis mode used for patients having a severe form of the disease may analyze more biological signal(s) and/or more generate more frequent measurement results than an analysis mode used for a patient with a more mild disease. In some examples, an analysis mode in which the detection device 504 is operated may be set from a plurality of predetermined analysis modes according to the severity of disease of the user associated with the detection device 504. The analysis mode in which the detection device 504 is operated may be reset (e.g., changed) based on predetermined conditions—e.g., predetermined change conditions or also referred to as predetermined environmental conditions.

The storage 522 may include change condition data 530 which may specify certain predetermined conditions which may cause a change in analysis mode used by the detection device 504. For example, the change condition data 530 may associate particular analysis modes with a particular time, temperature, activity of a user, or other conditions.

While shown as all stored in a same storage 522 in FIG. 5, the mode data 524, executable instructions for signal analysis mode(s) 526, and change condition data 530 may be stored together or separately, and/or may be distributed across multiple computer readable media. The configuration is quite flexible. Generally, the mode data 524, executable instructions for signal analysis mode(s) 526, and change condition data 530 may be electronically accessible by the microprocessor 520, wherever they are stored.

Generally, then storage 522 may store a plurality of predetermined analysis modes. Each of the analysis modes may be associated, for example, with a severity of disease. A selected analysis mode may be selected based on the severity of disease of a user associated with (or to be associated with) the detection device 504. The detection device 504 may then perform analysis and transmission in accordance with the selected analysis mode. The storage 522 may store determination algorithms (e.g., as part of executable instructions for signal analysis mode(s) 526) used for analysis by the microprocessor 520 of a variety of biological signals.

Examples of detection devices described herein may include a transmitter, such as transmitter 510. The transmitter 510 may include, for example, one or more antenna(s) and/or circuitry for transmitting data. The transmitter 510 may receive data (e.g., one or more measurement results) from the microprocessor 520 and may transmit the data to another computing device. The transmissions may occur in accordance with the selected analysis mode. The transmitter 510 may transmit data using wired or wireless methods. In some examples, the transmitter 510 may be capable of transmission using a long-range wireless communication method and a short-range wireless communication method. Examples of a long-range wireless communication method include communication over a network (e.g., Internet). Using the long-range wireless communication method, the transmitter 510 may, for example, transmit radio waves over a distance (e.g., several kilometers) by using radio frequencies (e.g., 920 MHz). Examples of a short-range wireless communication method include Bluetooth or NFC communication. In some examples, the transmitter 510 may include two transmitters—one configured for short-range wireless communication and another configured for long-range wireless communication. The transmitter 510 may communicate with any of a variety of other computing devices, including but not limited to one or more servers, computers, laptops, desktops, tablets, mobile phones, appliances, and/or medical equipment. In some examples, the transmitter 510 may communicate with one or more computing devices described herein (e.g., the computing devices 30 of FIG. 1). The computing device may in turn communicate with a centralized management device (e.g., the computing device 30 of FIG. 1 may communicate with the centralized management device 40 of FIG. 1). In some examples, the transmitter 510 may communicate with one or more centralized management devices described herein, such as centralized management device 40 of FIG. 1.

In some examples, the detection device 504 may, in accordance with the executable instructions for signal analysis mode(s) 526, made a determination regarding communication capabilities between the detection device 504 and the computing device to which the transmitter 510 may transmit. The detection device 504 (e.g. using microprocessor 520 executing executable instructions for signal analysis mode(s) 526) may select the short-range wireless communication method or the long-range wireless communication method in accordance with the determination. For example, if the intended recipient of the communication is determined to only have short-range wireless communication methods (or to prefer such methods), then the short-range wireless communication method may be used, and vice versa. In some examples, the detection device may select the communication method (e.g., the short-range wireless communication method or the long-range wireless communication method) based, at least in part, on one or more measurement results provided by the microprocessor 520.

Examples of detection devices described herein may include a power supply, such as power supply 512. The power supply 512 may provide power to all or some of the components of the detection device 504. The power supply 512 may be implemented using one or more batteries and/or energy harvesting circuitry. In some examples, an analysis mode of the detection device 504 may be selected based on available power at the detection device 504, e.g., a power state of the power supply 512. For example, an analysis mode specifying a lower frequency (e.g., less frequent occurrence) of data transmission may be selected if available power at the power supply 512 is below a threshold.

Examples of detection devices described herein may include additional sensors, such as sensor(s) 514. Sensor(s) 514 which may be used include, but are not limited to, one or more temperature sensors (e.g., to measure a temperature under clothing of a user), positional sensors (e.g., accelerometers, gyroscopes, GPS sensors, inertial sensors), pH sensors, moisture sensors, optical sensors, respiration sensors, and/or activity sensors. The sensor(s) 514 may be in electrical communication with the measurement circuitry 518 and/or the microprocessor 520.

Signals from the sensor(s) 514 may be used to select an particular analysis mode for use by the detection device 504. For example, change condition data 530 may include one or more thresholds or criteria for changing modes based on sensor data input. For example, based on a reading from one or more of the sensor(s) 514, the detection device 504 may change analysis modes in accordance with the executable instructions for signal analysis mode(s) 526. For example, the mode may be changed responsive to a position, movement, or location of the detection device as indicated by the sensor(s) 514. The sensor(s) 514 may indicate an activity of the user, and the analysis mode may be selected and/or changed based on the activity.

Examples of detection devices described herein may include one or more timers, such as timer 516. Signals from the timer 516 may be used to select an particular analysis mode for use by the detection device 504. For example, based on a time provided by the timer 516, the detection device 504 may change analysis modes in accordance with the executable instructions for signal analysis mode(s) 526.

Signals provided by the timer 516 and/or sensor(s) 514 may be provided to the transmitter 510 (e.g., directly and/or using the measurement circuitry 518 and/or the microprocessor 520). The transmitter 510 may accordingly transmit timer and/or sensor signals—either alone or in combination with other transmissions, such as measurement results described herein.

Examples of detection devices described herein may include a user interface, such as interface 528 of FIG. 5. The interface 528 may be implemented using, for example, one or more buttons, switches (e.g., a changeover switch), touchscreens, keyboard, mouse, or combinations thereof. In some examples, an operator (e.g., a patient and/or a medical service provider) may select and/or change an analysis mode of the detection device by providing an input to interface 528.

During operation, the measurement circuitry 518 may receive one or more signals provided by electrode 502 and/or electrode 506. The measurement circuitry 518 may measure a biological signal of a user—e.g., a heart rate, an electrocardiogram, or combinations thereof, based on the signals from the electrodes. The microprocessor 520, in accordance with executable instructions for signal analysis mode(s) 526, may analyze the biological signal in accordance with a selected analysis mode. Measurement results generated may be provided to the transmitter 510.

In some examples, the detection device 504 may include a timer 516 which measures time, a positional sensor to detect a position of the user utilizing the detection device 504, a temperature sensor to measure an environmental temperature inside clothes of the user, and an activity sensor for measuring human body activities of the user. The activity sensor may include, for example, an accelerometer and/or a respiration sensor. One or more measurement signals as a result of analyzing the biological signal of the user and respective signals of the timer, the positional sensor, the temperature sensor, and/or the activity sensor may be provided from the transmitter 510 to another computing device (e.g., to a centralized management device through a computing device, such as computing device 30 of FIG. 1).

Figure 6:
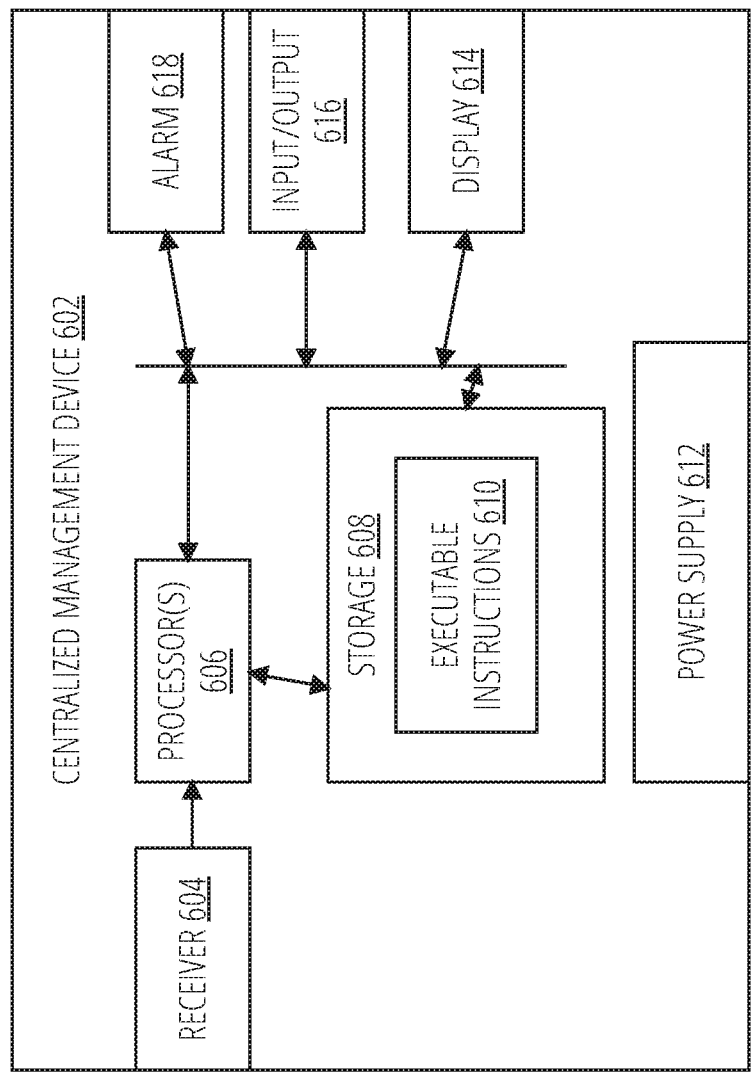
FIG. 6 is a schematic illustration of a centralized management device arranged in accordance with examples described herein.

FIG. 6 is a schematic illustration of a centralized management device arranged in accordance with examples described herein. The centralized management device 602 includes receiver 604, processor(s) 606, storage 608, power supply 612, display 614, input/output 616, and alarm 618. The storage 608 may store executable instructions 610. Additional, fewer, and/or different components may be used in other examples.

The centralized management device 602 may be used to implement and/or may be implemented by any centralized management device described herein, including the centralized management device 40 shown in FIG. 1 and FIG. 2. The centralized management device 602 may be implemented using a computing system, such as a computer, laptop, desktop, tablet, mobile phone, appliance, equipment, or combinations thereof.

Examples of centralized management devices described herein may include a receiver, such as receiver 604 of FIG. 6. The receiver may receive measurement results described herein from one or more detection devices and/or from one or more communication devices. For example, the receiver 604 may receive measurement results from the computing devices 30 shown in FIG. 1 and FIG. 2. In some examples, the receiver 604 may receive measurement signals from one or more detection devices 10 described herein. The receiver 604 may be able to receive signals using a long-range wireless communication method (e.g., over a network, such as the Internet). Multiple receivers may be provided in some examples of centralized management devices. For example, one receiver may receive signals using a long-range wireless communication method and another receiver may receive signals using a short-range wireless communication method (e.g., Bluetooth and/or NFC). The receiver 604 may be implemented, for example, using a Wi-Fi receiver, a Bluetooth receiver, an NFC receiver, or combinations thereof.

Examples of centralized management devices described herein may include one or more processor(s), such as processor(s) 606 of FIG. 6. Any number or variety of processors may be used, including one or more central processing units (CPUs), controllers, multi-core processors, and/or logic circuitry including application specific integrated circuits (ASICs) and/or field programmable gate arrays (FPGAs).

Examples of centralized management devices described herein may include storage, such as storage 608 of FIG. 6. The storage may be implemented using, for example, one or more computer readable media (e.g., memory, read only memory (ROM), random access memory (RAM), flash, solid state drives, secure digital (SD) card, or combinations thereof). The storage 608 may be encoded with executable instructions, such as executable instructions 610 which, when executed by the processor(s) 606, may cause the centralized management device 602 to perform actions described herein. For example, the centralized management device 602 may perform various types of analyses based on the measurement results received from detection devices. As another example, the centralized management device 602 may provide various types of alarms based on the measurement results received from detection devices in accordance with the executable instructions 610.

Examples of centralized management devices described herein may include a power supply, such as power supply 612 of FIG. 6. The power supply 612 may be implemented using, for example, one or more AC and/or DC connections and/or supplies. The power supply 612 may be implemented using one or more batteries and/or power harvesting circuitry. The power supply 612 may provide all or portions of power used by the receiver 604, processor(s) 606, storage 608, display 614, and/or other components of the centralized management device 602.

Examples of centralized management devices described herein may include one or more displays, such as display 614 of FIG. 6. The display 614 may be implemented, for example, using one or more light emitting diode (LED) displays, plasma displays, liquid crystal displays (LCDs), or combinations thereof. Other displays may be used in other examples. The display 614 may be in electronic communication with processor(s) 606 and/or storage 608. The display 614 may display measurement results received by the receiver 604 and/or processed by the processor(s) 606 as described herein. For example, the display 614 may display measurement results received from a plurality of detection devices. The measurement results may be received by the receiver 604 directly from the plurality of detection devices and/or may be received through one or more intermediate computing devices (e.g., computing devices 30 of FIG. 1 and FIG. 2). In some examples, the display 614 may display a plurality of measurement results (e.g., pertaining to a disease, such as heart disease, of the users U of FIG. 1 and FIG. 2). The measurement results may be displayed, for example in a list associating the measurement results with each respective user. In some examples, the display 614 may display messages, e.g., alarms. An alarm screen may be displayed by the display 614 in some examples.

Additional and/or different input and/or output devices may be provided in examples of centralized management devices, such as input/output 616. Examples include mice, keyboards, network interfaces, buttons, touchscreens, or combinations thereof. The input/output 616 may be used, for example, to activate applications included in the centralized management device and/or acknowledge alarms or otherwise interact with the centralized management device 602.

Examples of centralized management devices described herein may include one or more alarms, such as alarm 618. Alarms in some examples may be implemented using messages displayed on a display, such as display 614. In some examples, the alarm 618 includes one or more speakers to provide an audible alarm, such as one or more tones or voice messages. In some examples, alarm 618 includes one or more vibration activators to provide one or more vibrational alarms. The alarm 618 may provide an alarm, for example, in accordance with the executable instructions 610.

During operation, detection devices described herein may be attached to respective patients, e.g., users U. For example, the detection devices 10 shown in FIG. 1-FIG. 4 may be attached to respective users U. The detection devices may be implemented using the detection device 504 of FIG. 5. The analysis mode of each detection device may be selected according to the severity of disease (e.g., heart disease) of the user to which the device is attached. The setting may be performed, for example, by the user or another person (e.g., a medical provider). The user or the other person may select an analysis mode, for example, using an interface of the detection device (e.g., interface 528, such as a button and/or switch).

In some examples, the detection devices may have a default and/or initial analysis mode set to a mode associated with a mild degree of disease. This initial and/or default mode may be altered through an interface of the detection device (e.g., through interface 528). In some examples, the analysis mode for the detection device may be selected by another computing system (e.g., a computing device 30 as shown in FIG. 1-FIG. 4) or a different computing system. For example, the detection device may receive a signal from another computing system indicative of a selected analysis mode for the user.

Examples of analysis modes will now be described. Detection devices described herein may be able to conduct analysis in accordance with a selected analysis mode (e.g., using executable instructions for signal analysis mode(s) 526 of FIG. 5). Data which may specify each of the analysis modes (e.g., mode data 524) may be stored in storage of the detection device.

In some examples, the detection devices may operate in one of three analysis modes—a first analysis mode M1, a second analysis mode M2, and/or a third analysis mode M3. These analysis modes may be associated with respective severity of disease (e.g., heart disease) of the users U. The first analysis mode M1 may be associated with a mild degree of heart disease, the second analysis mode M2 may be associated with a moderate degree of heart disease, and the third analysis mode M3 may be associated with a severe degree of heart disease.

In a detection device to be attached to a user having a mild degree of heart disease, the first analysis mode M1 may be selected. In another detection device to be attached to a user having a moderate degree of heart disease, the second analysis mode M2 may be selected. In a detection device to be attached to a user U having a severe degree of heart disease, the third analysis mode M3 may be selected. The selection may be made in some examples before the detection device is attached to the user, and in some examples the selection may be made after the detection device is attached to the user.

Examples of the analysis performed in the analysis modes M1, M2, and M3, and measurement results transmitted during those modes, are now described. Note that other analysis modes may be used in other examples setting different measurement results to generate and/or transmit. Referring to the detection device 504, note that the executable instructions for signal analysis mode(s) 526 may include instructions for generating and transmitting measurement results in accordance with mode M1, M2, and/or M3. Moreover, mode data 524 may include data describing modes M1, M2, and M3.

In an example of a first analysis mode M1 associated with a mild degree of disease, the detection device may analyze heart rates and/or electrocardiograms. The detection device may determine whether the heart rate has deviated from a predetermined threshold range. The predetermined threshold range for mode M1 may be stored, for example, in mode data 524. In the first analysis mode M1, the detection device may transmit heart rates, electrocardiograms, and/or threshold-value determination results. The transmission may be made periodically, e.g., every 10 minutes.

In an example of a second analysis mode M2 associated with a moderate degree of disease, the detection device may analyze heart rates and/or electrocardiograms. The detection device may determine whether the user has an irregular pulse based on the electrocardiogram. Criteria used to determine whether the pulse may be irregular may be stored, for example, in mode data 524. The detection device may transmit heart rates, electrocardiograms, and/or irregular-pulse determination results. The transmission may be made periodically, e.g., every 1 minute. Generally, the period between transmissions in a mode associated with moderate disease may be greater than the period between transmissions in a mode associated with mild disease.

In an example of a third analysis mode M3 associated with a severe degree of disease, the detection device may analyze heart rates and/or electrocardiograms. The detection device may determine whether the user has an irregular pulse based on the electrocardiogram. The detection device may transmit heart rates, electrocardiograms, and/or irregular-pulse determination results. The detection device may make transmissions continuously in mode M3. Generally, the period between transmissions in a mode associated with severe disease may be greater than the period between transmissions in a mode associated with moderate and/or mild disease.

At the time the detection device determines whether an irregular pulse is present, the analysis device may additionally analyze other parameters, including, but not limited to, asystole, ventricular fibrillation (VF), ventricular tachycardia (VT), tachycardia, bradycardia, atrial fibrillation (AF), ventricular premature contraction (VPC), a couplet (e.g., two continuous incidences) of VPC, an irregular RR (e.g., irregularity in intervals of electrocardiogram R-waves), and/or bigeminy (e.g., bigeminal pulse of VPC; a normal pulse and premature contraction are repeated).

Generally, asystole, VF and VT may be the most dangerous items from the above items, which may desirably receive fast (e.g., immediate) treatment. Tachycardia, Bradycardia, AF and VPC may be items which may not receive fast (e.g., immediate) treatment but desirably be monitored.

For example, in the determination of the irregular pulse in the second analysis mode M2, three analysis items of asystole, VF and VT may be used. In the determination of the irregular pulse in the third analysis mode M3, additional analysis items (e.g., 23 items) may be performed at the time of analyzing the irregular pulse including the above described items are used. The analysis items are not limited to 23 items and additional, fewer, and/or different analysis items may be used.

Accordingly, detection devices described herein may analyzing whether an abnormal waveform is contained in an electrocardiogram of the user based on the number of items to be used in that mode, in accordance with the executable instructions for signal analysis mode(s) 526, for example.

Figure 7A:
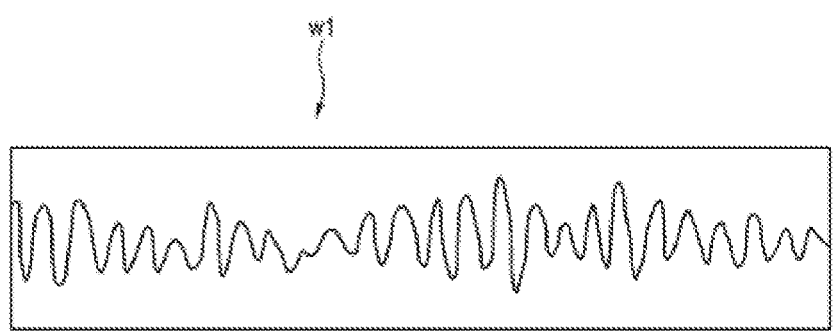
FIG. 7A is an example of an electrocardiogram at a time of ventricular fibrillation.
Figure 7B:
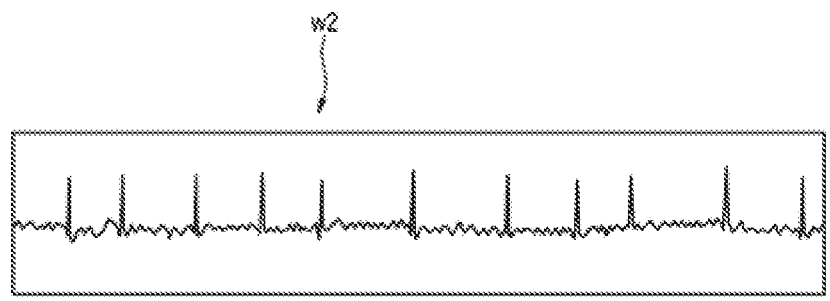
FIG. 7B is an example of an electrocardiogram at a time of atrial fibrillation.

FIG. 7A is an example of an electrocardiogram, e.g. waveform W1, at a time of ventricular fibrillation. FIG. 7B is an example of an electrocardiogram, e.g., waveform W2, at a time of atrial fibrillation. Detection devices described herein may perform analysis of electrocardiogram signals and/or data indicative of an electrocardiogram using a determination algorithm in accordance with a selected mode (e.g., as specified by executable instructions for signal analysis mode(s) 526). Examples of determination algorithms which may be used, include, for example, whether the heart rate per a unit time exceeds a prescribed value, and/or whether an outer shape or peak intervals of abnormal waveforms vary. In some examples, a determination of abnormality may be made also using other parameters such as a temperature, acceleration, and/or respiration, which may be obtained from other sensors of the detection device described herein. In this manner, detection devices described herein may discriminate waveform variation due to a biological abnormality (e.g., a heart condition) from variation due to tooth brushing or walking of the user. In this manner, accuracy of the determination may be increased. While abnormalities have been described as detected by detection devices, in some examples, abnormalities may be detected and/or determined by computing devices and/or centralized management devices described herein (e.g., by centralized management device 602 in accordance with executable instructions 610).

Examples of monitoring patients using systems described herein is now described. For users having a mild degree of disease, the detection device attached to the user may be operated in accordance with an analysis mode indicative of mild disease (e.g., analysis mode M1). For example, the detection device may perform the analysis of the first analysis mode M1 described herein every prescribed time (e.g., 10 minutes). A detection signal including various measurement results (e.g., the heart rate and a determination result of the heart rate) may be transmitted to a centralized management device (e.g., centralized management device 40 and/or centralized management device 602). The transmission may occur through one or more computing devices, such as computing device 30.

Heart rates of users and/or determination results may be displayed on a display of the centralized management device (e.g., on display 614 of FIG. 6). When the determination result of the heart rate is a determination indicating that the heart rate is deviated from a threshold range, the centralized management device may provide an alarm (e.g., an auditory, visual, and/or vibratory alarm, such as a voice message) which may inform medical workers or others of the result.

For users having a moderate degree of disease, the detection device attached to the user may be operated in accordance with an analysis mode indicative of moderate disease (e.g., analysis mode M2). For example, the detection device may perform the analysis of the second analysis mode M2 described herein every prescribed time (e.g., every 1 minute). A detection signal including various measurement results (e.g., the heart rate and a determination result of the irregular pulse) may be transmitted to a centralized management device (e.g., centralized management device 40 and/or centralized management device 602). The transmission may occur through one or more computing devices, such as computing device 30.

Heart rates and/or determination results may be displayed on a display of the centralized management device (e.g., on display 614 of FIG. 6). When the determination result of the irregular pulse is a determination indicating that an abnormal waveform is contained in the electrocardiogram, the centralized management device may provide an alarm (e.g., an auditory, visual, and/or vibratory alarm, such as a voice message) which may inform medical workers or others of the result.

For users having a severe degree of disease, the detection device attached to the user may be operated in accordance with an analysis mode indicative of severe disease (e.g., analysis mode M3). For example, the detection device may perform the analysis of the third analysis mode M3 described herein every prescribed time (e.g., continuously). A detection signal including various measurement results (e.g., the heart rate and a determination result of the irregular pulse) may be transmitted to a centralized management device (e.g., centralized management device 40 and/or centralized management device 602). The transmission may occur through one or more computing devices, such as computing device 30.

Heart rates and/or determination results may be displayed on a display of the centralized management device (e.g., on display 614 of FIG. 6). When the determination result of the irregular pulse is a determination indicating that an abnormal waveform is contained in the electrocardiogram, the centralized management device may provide an alarm (e.g., an auditory, visual, and/or vibratory alarm, such as a voice message) which may inform medical workers or others of the result.

Figure 8:
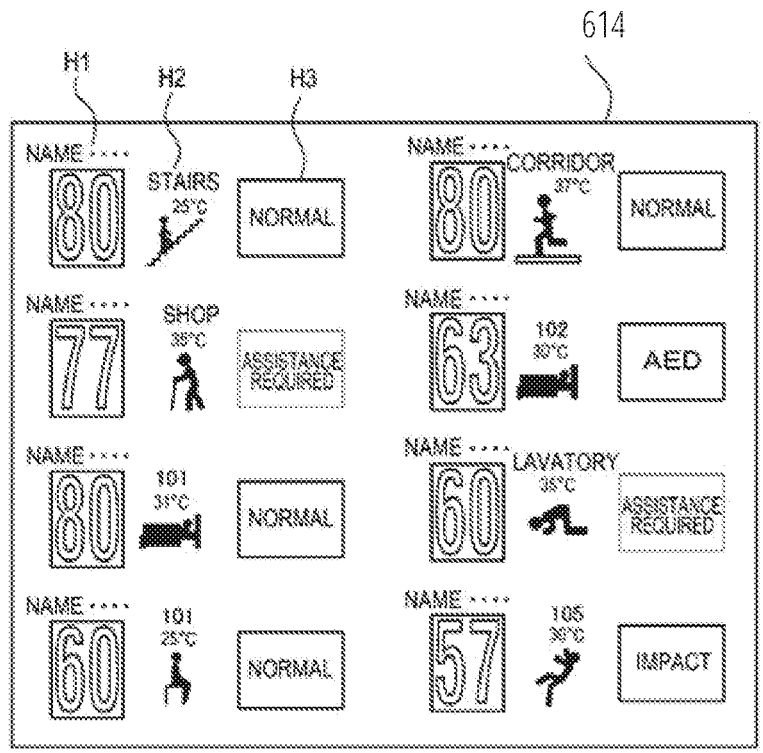
FIG. 8 is a schematic illustration of a display of a centralized management device arranged in accordance with examples described herein.

FIG. 8 is a schematic illustration of a display of a centralized management device arranged in accordance with examples described herein. The illustration of FIG. 8 may be displayed, for example on display 614 of the centralized management device 602 of FIG. 6 in some examples.

As shown in FIG. 8 a collection, e.g., list, of a plurality of measurement results concerning heart disease of users U is displayed on the display 614 of a centralized management device. For example, a heart rate H1, whereabouts H2 and state H3 of each user U may be displayed. Each user may be located in a same area, e.g., sickroom 2 of FIG. 1 for example.

The heart rate H1 may be displayed together with a name or other identifier of the user U. The heart rate may be displayed as a numerical value. When the heart rate is deviated from the threshold range, an alarm may be visually indicated, such as by having a frame of the heart rate H1 displayed, or the heart rate H1 itself displayed in an alarm color (for example, yellow or red).

Whereabouts H2 may be displayed. For example, characters indicating a current location of the user U may displayed. In some examples, a posture or movement of the user U may be displayed as an image (e.g., a stick person and/or cartoon). For example, whereabouts H2 may be displayed as characters such as "stairs" "shop" and/or "lavatory" or a sickroom or other area identifier (e.g., a number) may be displayed indicating a current location of the user U. In some examples, an environmental temperature inside clothes of the user U may additionally or instead be displayed as whereabouts H2.

State H3 may be displayed. For example, characters indicating a condition of the user U, e.g., characters indicating treatment contents and/or status of the user U may be displayed. In the state display H3, "normal", "assistance required" and so on are displayed as conditions of the user U, characters of "AED" and the like may be displayed when treatment by an automated external defibrillator (AED) is indicated, and characters of "IMPACT" and the like may be displayed when the user U receives an impact due to collision with a door, floor, or the like. Moreover, a frame that surrounds the characters indicative of state may be displayed, and the color of the frame and/or characters may change according to the situation. For example, the frame is displayed in green to indicate a normal state and the frame may be displayed in yellow or red according to a degree of emergency at the time of emergency.

Examples of setting a detection device to utilize a particular analysis mode, and monitoring a user using a particular analysis mode are described herein. Further, analysis modes may be changed (e.g., reset) in some examples. The analysis mode of a detection device may in some examples automatically be changed (e.g., reset) according to predetermined conditions (e.g., a predetermined environmental condition). For example, the detection device 504 may change analysis conditions in accordance with executable instructions for signal analysis mode(s) 526 and change condition data 530.

Generally, a variety of situations may be identified in advance for which is may be desirable for the detection device to change analysis modes based on the condition of the user and/or the environment. On occurrence of the situation, the analysis mode may change. For example, the executable instructions for signal analysis mode(s) 526 may include instructions for recognizing a situation is occurring or has occurred and to change the analysis mode based on identification of the situation.

In some examples, the analysis mode may be changed based on time. For example, the analysis mode used by detection device 504 may change based on a time provided by the timer 516. For example, a change in time of day and/or time zone may in some examples cause a change in analysis mode. For example, an analysis mode for disease of high severity may be selected during a time of day and/or a time zone in which a symptom may generally be considered to be worsened. An analysis mode associated with a low severity of disease may be selected during a time of day and/or time zone in which the symptom may generally be considered to be reduced.

In some examples, the analysis mode may be changed based on time and in consideration of a number of medical workers present at the time. For example, the analysis mode associated with severe disease may be selected when the time is indicative of a time when fewer medical workers may be present (e.g., a night shift). The analysis mode associated with a low severity of disease may be selected when the time indicates a time when a larger number of medical workers may be present (e.g., during a day shift).

In some examples, the analysis mode may be changed based on location and/or connectivity status. In some examples, a detection device may change analysis mode based on information received from a location sensor (e.g., a GPS system). In some examples, the analysis mode may be automatically reset in accordance with a destination of the user. In some examples, an analysis mode associated with high disease severity may be selected when the user U moves to a location (e.g., a shop) where a medical worker is not present, while an analysis mode associated with low severity of disease may be selected when the user U moves to a location (e.g., a hospital, room 2) where a medical worker is present.

In some examples, when no positional information is available—e.g., when a location sensor of the detection device is malfunctioning and/or when the detection device is not in a position capable of receiving signals (e.g., GPS signals) for positional information, the analysis mode may be changed to an analysis mode associated with a high severity of disease (e.g., an analysis mode having an increased frequency of transmissions). In some examples, when no positional information is available, an alarm may be provided at the centralized management device.

In some examples, when the detection device is in a location where it cannot perform communication with another computing device or the centralized management device, the detection device may also switch the analysis mode to the analysis mode associated with a high severity of disease, and further, an alarm may be given to surrounding medical workers by noise, light, a message and so on at the centralized management device.

In some examples, when the detection device is moved to a position where the detection device is not capable of performing communication with another computing device or the centralized management device, a communication method utilized by the detection device, the another computing device, or the centralized management device (e.g., detection device 10, computing device 30, and/or centralized management device 40) may be changed. Changing the communication method may facilitate re-establishing communication with the detection device. For example, the detection device computing device, and/or centralized management device may utilize a transmitter and/or transmission method for performing communication in a wider range (e.g., over a longer distance).

In some examples, when the detection device 10 detects that asystole, VF or VT in the analysis items belonging to the analysis mode associated with a high severity of disease is in an dangerous state and when the detection device is in a position where the detection device is not capable of performing communication with another computing device or the centralized management device, the communication may be re-established by changing the communication method used by the transmitter e.g., the transmitter 510, for performing communication in a wider range (e.g., over a longer distance).

For example, the detection device (e.g., detection device 10 of FIG. 1 and/or detection device 504 of FIG. 5) may normally perform communication with another computing device (e.g., computing device 30), for example, in a range of several 10s of meters to several 100s of meters by using Bluetooth (e.g., operating at 2.4 GHz) as an example of a short-range wireless communication method. However, when the detection device detects that asystole, VF or VT in the analysis items of the analysis mode associated with a high severity of disease is in an dangerous state, it is also possible to establish a communication network of several ten kilometers by automatically switching the communication method to a long-range wireless communication method (e.g., operating at 920 MHz) to thereby switch the communication state to a state in which the communication with respect to the surrounding computing device or the centralized management device may be maintained more easily. In some examples, the detection device may be operated so as to establish communication in both frequency bands for short- and long-range communications (e.g., 2.4 GHz and 920 MHz). After the communication is established again, the detection device can inform another device of the dangerous state.

In some examples, the detection device may change (e.g., reset) the analysis mode using measurement results—e.g., of the heart rate or the electrocardiogram. For example, the analysis mode may be automatically reset in accordance with conditions of the user U which can vary from moment to moment. In some examples, the analysis mode may be switched to the analysis mode associated with heart disease of high severity when the heart rate exceeds a threshold value or an abnormal waveform is detected in the electrocardiogram. In some examples, the analysis mode may be switched to the analysis mode associated with heart disease of a low severity when the heart rate is stable for a long period of time and an abnormal waveform is not detected in the electrocardiogram.

In some examples, the detection device may change (e.g., reset) the analysis mode using the environmental temperature inside clothes of the user. The temperature inside clothes of the user may be measured, for example, by a temperature sensor of the detection device. For example, the analysis mode may be automatically reset in accordance with variation in environmental temperature of the user U. For example, the analysis mode may be switched to the analysis mode associated with heart disease of high severity when it is determined, from temperature change, that the user U is moved to outside of the room 2 or the ward 1 of FIG. 1. The analysis mode may be switched to the analysis mode associated with heart disease of low severity when it is determined that the user U is present in the room 2 of FIG. 1 where the temperature is fixed because there is no change in temperature measured by the temperature sensor.

In some examples, the detection device may change (e.g., reset) the analysis mode using user activities, e.g., measured by an activity sensor of the detection device. For example, the analysis mode may be automatically reset in accordance with human body activities of the user U. For example, the analysis mode may be switched to the analysis mode associated with disease of high severity when it is determined that the user U falls down (e.g., at stairs, at a corridor, at a lavatory or the like) based on a detection signal provided by an activity sensor, which may include, for example, an accelerometer, a respiration sensor, etc. Criteria for detecting a fall or other activity and/or executable instructions for detecting a fall or other activity may, for example, be stored at the detection device (e.g., in storage 522 of FIG. 5).

An activity sensor of the detection device may include for example, an accelerometer, an atmospheric sensor, a respiration sensor that measures a respiration of the user U, an SpO2 sensor that measures a percutaneous arterial blood oxygen saturation (SpO2) of the user U, and/or other sensors. Variation in human body activities of the user U may be detected based on these sensors and the variation may be used to make a change to the analysis mode. Pattern analysis of sensor signals may be used by the detection device to detect variation in user activity.

In some examples, a detection device may change (e.g., reset) the analysis mode responsive to user input, e.g., through an input from by operation of the interface 528 of FIG. 5 and/or input/output 616 of FIG. 6. In this manner, the analysis mode may be selected and/or changed by, for example, a medical worker operating the interface 528 in accordance with a condition of the user U.

In this manner, an analysis mode for detection devices described herein may be selected from a plurality of predetermined analysis modes according to the severity of disease of the user. Accordingly, a medical worker or other observer may select the analysis mode in which the detection device is operated in accordance with the severity of heart disease of the user U at the time of attaching the detection device to a body surface of the user U. The medical worker can select, for example, the first analysis mode M1 associated with a low severity of disease and having a relatively smaller number of analysis items. Or the medical worker can select the second analysis mode M2 or the third analysis mode M3 in which the number of analysis items is larger and the analysis modes are associated with a moderate or high severity of disease, respectively.

Accordingly, as described herein, medical services (e.g., monitoring and responsive services) may be provided personalized for the users using detection devices described herein.

Detection devices described herein may have a plurality of analysis modes, including the second analysis mode M2 and the third analysis mode M3 described herein which may include analyzing whether an abnormal waveform indicating ventricular fibrillation or atrial fibrillation is contained in an electrocardiogram or not when the detection device is attached to the body surface of the user U.

In some examples, the analysis mode may be automatically reset according to the situation by setting change conditions in accordance with situations and/or environmental variations. Accordingly, using detection devices described herein, accurate monitoring of users may be achieved and loads of medical workers may be reduced. Examples described herein may also save power of detection devices by avoiding unnecessary operation of analysis modes with higher power consumption (e.g., modes M2 and/or M3).

The analysis mode may be automatically changed (e.g., reset) in accordance with variation in severity of disease of the user according to a time by using time measured by a timer as the change condition of the analysis mode. The analysis mode can be also automatically changed in accordance with a work shift of medical workers. For example, the analysis mode may be switched to the analysis mode associated with disease of high severity in the night shift when the number of medical workers is small, which may provide for increased monitoring and reduced loads for medical workers.

The analysis mode may be automatically changed (e.g., reset) in accordance with a location of the user U using positional information of the detection device as the change condition of the analysis mode. The analysis mode may be switched to the analysis mode associated with disease of high severity when the user U moves to a shop or the like where a medical worker is not present, which may provide for increased monitoring and reduced loads for medical workers.

The analysis mode may be automatically changed (e.g., reset) in accordance with conditions of the user U as a patient which can vary from moment to moment by using measurement results (e.g., biological signals such as the heart rate or the electrocardiogram) measured by the detection device. For example, the analysis mode may be switched to the analysis mode associated with disease of high severity when the heart rate exceeds a threshold value or an abnormal waveform is detected in the electrocardiogram, which may provide for increased monitoring and reduced loads for medical workers.

In some examples, it may be possible to determine that a user has moved to the outside of an area (e.g., ward, hospital) based on variation in environmental temperature. For example, the environmental temperature inside clothes of the user, which may be measured by a temperature sensor of the detection device, may be used as the change condition for the analysis mode. The analysis mode may be automatically changed in accordance with the status. Accordingly, this may provide for increased monitoring and reduced loads for medical workers.

In some examples, the analysis mode may be automatically changed (e.g., reset) in accordance with variation in human body activities of the user U by using human body activities of the user U, which may be measured by an activity sensor, as the change condition for the analysis mode. For example, the analysis mode may be switched to the analysis mode associated with disease of high severity when the user U falls down. Accordingly, this may provide for increased monitoring and reduced loads for medical workers.

In some examples, an interface may be used to select a desired analysis mode, which may allow a medical worker to manually select an analysis mode.

Accordingly, examples of monitoring systems and detection devices described herein may assist in providing medical services suitable for respective patients. Medical workers or other observers may check analysis results for multiple patients displayed (e.g., in a list) on a display of a centralized management device. This may allow for effective monitoring of a location where multiple patients having heart disease are located, which may also reduce loads of medical workers.

Examples described herein have been described in the context of heart disease. However, other diseases may be monitored using systems and devices described herein, and biological signals used are not limited to heart rates and/or electrocardiograms.

Examples described herein are not intended to be limiting and modifications, improvements and so on may occur. Materials, shapes, sizes, numerical values, states, numbers, arrangement places and the like of respective components described herein are arbitrary and are not limiting of the claimed technology.

From the foregoing it will be appreciated that, although specific embodiments have been described herein for purposes of illustration, various modifications may be made while remaining with the scope of the claimed technology.

Examples described herein may refer to various components as "coupled" or signals as being "provided to" or "received from" certain components. It is to be understood that in some examples the components are directly coupled one to another, while in other examples the components are coupled with intervening components disposed between them. Similarly, signal may be provided directly to and/or received directly from the recited components without intervening components, but also may be provided to and/or received from the certain components through intervening components.

What is claimed is:

1. A device comprising:
   measurement circuitry configured to measure a biological signal of a user when the device is carried by the user and output a measurement signal based, at least in part, on the biological signal measured;
   at least one processor coupled to the measurement circuitry;
   at least one non-transitory computer readable media encoded with instructions which, when executed, cause the device to operate in accordance with a selected analysis mode of a plurality of analysis modes to analyze the measurement signal and provide a result of determination, wherein each analysis mode of the plurality of analysis modes is associated with a respective one of a plurality of severities of a disease of the user, wherein the at least one processor is configured to select the analysis mode associated with a severity of a disease of the user, from the plurality of analysis modes stored in the media, and the at least one processor is further configured to execute select determination algorithms on the measurement signal in accordance with the selected analysis mode; and
   a transmitter coupled to the at least one processor, the transmitter configured to transmit, by a transmission method defined in the selected analysis mode, the result of determination generated in accordance with the selected analysis mode to another computing device.

2. The device of claim 1, wherein the at least one non-transitory computer readable media is configured to store data pertaining to the plurality of analysis modes.

3. The device of claim 1, wherein the measurement circuitry is configured to measure the biological signal when the device is attached to a body surface of the user.

4. The device of claim 1, wherein the instructions further include instructions which, when executed, cause the device to change the selected analysis mode based on at least one predetermined condition.

5. The device of claim 4, further comprising a timer coupled to the at least one processor, and wherein the at least one predetermined condition is based at least in part on a time measured by the timer.

6. The device of claim 4, further comprising a positional sensor coupled to the at least one processor, and wherein the at least one predetermined condition is based at least in part on a position of the device as indicated by the positional sensor.

7. The device of claim 4, wherein the at least one predetermined condition is based at least in part on the result of analysis.

8. The device of claim 4, further comprising a temperature sensor configured to measure a temperature under clothes of the user, and wherein the at least one predetermined condition is based at least in part on the temperature.

9. The device of claim 4, further comprising an activity sensor configured to measure an activity of the user, and wherein the at least one predetermined condition is based at least in part on the activity.

10. The device of claim 1, further comprising a user interface coupled to the at least one processor, and wherein the selected analysis mode is based, at least in part, on an input from the user interface.

11. The device of claim 10, wherein the user interface comprises a switch.

12. The device of claim 1, wherein the biological signal comprises an electrocardiogram.

13. The device of claim 12, wherein the instructions further cause the device to analyze whether an abnormal waveform indicative of ventricular fibrillation, atrial fibrillation, or combinations thereof, are contained in the electrocardiogram.

14. The device of claim 1, wherein the transmitter is configured to transmit using a short-range wireless communication method, a long-range wireless communication method, or combinations thereof, and wherein the instructions further include instructions for making a determination regarding communication capabilities between the device and the computing device and selecting the short-range wireless communication method or the long-range wireless communication method in accordance with the determination.

15. The device of claim 1, wherein the transmitter is configured to transmit using a short-range wireless communication method, a long-range wireless communication method, or combinations thereof, and wherein the instructions further include instructions for selecting the short-range wireless communication method or the long-range wireless communication method based, at least in part, on the result of analysis.

16. A system comprising:
    a plurality of detection devices, each of the plurality of detection devices configured to:
      be attached to a respective user;
      analyze a biological signal of the respective user;
      output a measurement signal based, at least in part, on the biological signal measured; and
      transmit, by a transmission method defined in a selected analysis mode of a plurality of analysis modes, at least one result of determination generated in accordance with the selected analysis mode, wherein each analysis mode of the plurality of analysis modes is associated with a respective severity of disease of the respective user, wherein each of the plurality of detection devices includes at least one processor and wherein the at least one processor is configured to select the analysis mode associated with the respective severity of a disease of the respective user, and the at least one processor is further configured to execute select types of determination algorithms on the measurement signal in accordance with the selected analysis mode;

a plurality of computing devices, each configured to receive the at least one result of determination from each of the plurality of detection devices in a respective subset of the plurality of detection devices, wherein each of the plurality of computing devices is configured to provide a result of analysis from the at least one result of determination received from each of the plurality of detection devices in the respective subset of the plurality of detection devices; and a centralized management device configured to communicate with the plurality of computing devices, wherein the centralized management device is configured to display at least one result of analysis from the result of analysis provided by each of the plurality of computing devices.

17. The system of claim 16, wherein each of the plurality of detection devices further includes:

at least one non-transitory computer readable media encoded with instructions which, when executed, cause the detection device to select the selected analysis mode from the plurality of analysis modes.

18. The system of claim 17, wherein the at least one non-transitory computer readable media is further configured to store data pertaining to the plurality of analysis modes.

19. The system of claim 16, wherein the selected analysis mode is selected based, at least in further part, on a predetermined environmental condition.

20. The system of claim 19, wherein the predetermined environmental condition comprises a time, a location of the respective user, an activity of the respective user, or combinations thereof.

21. A device comprising:

measurement circuitry configured to measure a biological signal of a user when the device is carried by the user and output a measurement signal based, at least in part, on the biological signal;

at least one processor coupled to the measurement circuitry;

at least one non-transitory computer readable media encoded with instructions which, when executed, cause the device to operate in accordance with a selected analysis mode of a plurality of analysis modes to analyze the measurement signal and provide a result of determination, wherein each analysis mode of the plurality of analysis modes is associated with a respective one of a plurality of severities of a disease of the user, wherein the at least one processor is configured to select the analysis mode associated with a severity of a disease of the user, from the plurality of analysis modes stored in the media, and the at least one processor is further configured to execute select determination algorithms on the measurement signal in accordance with the selected analysis mode; and a transmitter coupled to the at least one processor, the transmitter configured to transmit, by a transmission method defined in the selected analysis mode, the result of determination generated in accordance with the selected analysis mode to another computing device, wherein the media is configured to store determination algorithms used for analysis by the at least one processor, and the transmitter is further configured to transmit the result of determination with a frequency defined by the selected analysis mode.

* * * * *